US012629498B2

(12) United States Patent
Sieracki et al.

(10) Patent No.: US 12,629,498 B2
(45) Date of Patent: May 19, 2026

(54) TUBE SECUREMENT TAPE

(71) Applicant: Solventum Intellectual Properties Company, Maplewood, MN (US)

(72) Inventors: James M. Sieracki, Plymouth, MN (US); Krystal J. Scheibel, Minneapolis, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 909 days.

(21) Appl. No.: 17/636,915

(22) PCT Filed: Oct. 20, 2020

(86) PCT No.: PCT/IB2020/059861
§ 371 (c)(1),
(2) Date: Feb. 21, 2022

(87) PCT Pub. No.: WO2021/084382
PCT Pub. Date: May 6, 2021

(65) Prior Publication Data
US 2022/0355078 A1     Nov. 10, 2022

Related U.S. Application Data

(60) Provisional application No. 62/927,250, filed on Oct. 29, 2019.

(51) Int. Cl.
*A61M 25/02*     (2006.01)
*A61F 13/02*     (2024.01)
*A61F 13/0246*     (2024.01)

(52) U.S. Cl.
CPC ........... *A61M 25/02* (2013.01); *A61F 13/025* (2013.01); *A61F 13/0259* (2013.01);
(Continued)

(58) Field of Classification Search
CPC .......... A61M 25/02; A61M 2025/0253; A61M 2025/0246; A61M 2025/0206;
(Continued)

(56) References Cited

U.S. PATENT DOCUMENTS 3,389,827 A     6/1968   Abere et al.
3,645,835 A     2/1972   Hodgson et al.
(Continued)

FOREIGN PATENT DOCUMENTS

EP          2269548 A1    1/2011
WO      1990002578 A1    3/1990
(Continued)

OTHER PUBLICATIONS

International Search report for PCT International Application No. PCT/IB2020/059861 mailed on Jan. 20, 2021, 6 pages.

*Primary Examiner* — William R Carpenter
*Assistant Examiner* — Robert F Allen

(57) ABSTRACT

The disclosed securement tape strip comprises a tape having a midsection, a stabilizing section, and a wrapping strip. The tape strip has an adhesive along the midsection to adhere the tape strip to a substrate. The wrapping strip can include an adhesive for wrapping the wrapping strip around a device to hold the device securely in place on the substrate. The tape strip can include a perforation set along the midsection. The perforation set can be useful in removal of the tape.

12 Claims, 4 Drawing Sheets

(52) U.S. Cl.
CPC .............. *A61M 2025/0206* (2013.01); *A61M 2025/0213* (2013.01); *A61M 2025/0246* (2013.01); *A61M 2025/0253* (2013.01); *A61M 2025/026* (2013.01); *A61M 2025/0266* (2013.01); *A61M 2025/0273* (2013.01)

(58) Field of Classification Search
CPC .. A61M 2025/0213; A61M 2025/0266; A61M 2025/0273; A61M 2025/026; A61F 13/025; A61F 13/0259; A61F 13/05; A61F 2013/00412
See application file for complete search history.

(56) References Cited

U.S. PATENT DOCUMENTS

| | | | |
|---|---|---|---|
| 4,112,213 A | 9/1978 | Waldman et al. | |
| 4,310,509 A | 1/1982 | Berglund et al. | |
| 4,323,557 A | 4/1982 | Rosso et al. | |
| 4,460,356 A * | 7/1984 | Moseley ............... | A61M 25/02 604/180 |
| 4,472,480 A | 9/1984 | Olson | |
| 4,490,141 A * | 12/1984 | Lacko .................... | A61M 25/02 128/DIG. 26 |
| 4,534,762 A * | 8/1985 | Heyer ................... | A61M 25/02 128/DIG. 26 |
| 4,595,001 A | 6/1986 | Potter et al. | |
| 4,737,410 A | 4/1988 | Kantner | |
| 4,823,789 A * | 4/1989 | Beisang, III .......... | A61M 25/02 128/911 |
| 5,088,483 A | 2/1992 | Heinecke | |
| 5,230,701 A | 7/1993 | Meyer et al. | |
| 5,304,146 A * | 4/1994 | Johnson ................ | A61M 25/02 128/DIG. 26 |
| 5,306,256 A * | 4/1994 | Jose ...................... | A61M 25/02 128/DIG. 26 |
| 5,546,938 A | 8/1996 | McKenzie et al. | |
| 6,607,799 B1 | 8/2003 | Heinecke et al. | |
| 7,294,752 B1 | 11/2007 | Propp | |
| 7,524,307 B2 * | 4/2009 | Davis ................... | A61M 25/02 604/174 |
| 7,626,070 B2 | 12/2009 | Propp | |
| 7,723,561 B2 | 5/2010 | Propp | |
| 8,053,623 B2 | 11/2011 | Propp | |
| 8,157,770 B2 * | 4/2012 | Elwell ................... | A61M 25/02 604/177 |
| 8,212,101 B2 | 7/2012 | Propp | |
| 9,320,840 B2 * | 4/2016 | Angel ................... | A61M 1/741 |
| 9,604,031 B2 | 3/2017 | Heinecke et al. | |
| 2005/0020957 A1 | 1/2005 | Lebner et al. | |
| 2005/0171482 A1 * | 8/2005 | Russo ................... | A61M 25/02 128/DIG. 26 |
| 2005/0261623 A1 | 11/2005 | Propp et al. | |
| 2009/0187130 A1 | 7/2009 | Asmus et al. | |
| 2009/0211573 A1 * | 8/2009 | Russo ............... | A61M 16/0488 128/207.14 |
| 2009/0292256 A1 * | 11/2009 | Cubberly .............. | A61M 25/02 604/180 |
| 2010/0081996 A1 * | 4/2010 | Fink ...................... | A61M 25/02 604/180 |
| 2010/0106095 A1 * | 4/2010 | Vitaris .................. | A61M 25/02 604/177 |
| 2010/0199997 A1 * | 8/2010 | McInnes ............... | A61M 25/02 128/207.14 |
| 2011/0112492 A1 * | 5/2011 | Bharti ..................... | A61F 13/05 604/319 |
| 2011/0245778 A1 * | 10/2011 | Chawki ................. | A61M 25/02 604/180 |
| 2012/0029435 A1 * | 2/2012 | Gutierrez Del Rio ...................... A61M 16/0497 604/179 |
| 2012/0109070 A1 * | 5/2012 | Elsamahy ............. | A61M 25/02 604/179 |
| 2012/0203182 A1 * | 8/2012 | Kay .................... | A61F 13/0269 604/180 |
| 2013/0150796 A1 * | 6/2013 | Souza ................... | A61M 25/02 604/180 |
| 2013/0165864 A1 * | 6/2013 | Fink ...................... | A61M 25/02 604/174 |
| 2014/0039401 A1 * | 2/2014 | Kerr ...................... | A61M 25/02 604/180 |
| 2014/0155833 A1 * | 6/2014 | Gugliotta .............. | A61M 25/02 604/179 |
| 2015/0209543 A1 * | 7/2015 | Disanza ............ | A61M 16/0875 128/200.24 |
| 2015/0209552 A1 * | 7/2015 | Bierman ............... | A61M 39/10 604/500 |
| 2016/0015570 A1 | 1/2016 | Heinecke et al. | |
| 2016/0067451 A1 * | 3/2016 | Kyvik .................... | A61M 25/02 604/500 |
| 2016/0184553 A1 * | 6/2016 | Fleischer .............. | A61M 25/02 604/179 |
| 2017/0326340 A1 * | 11/2017 | Howell ............. A61F 13/01034 |
| 2018/0050175 A1 | 2/2018 | Souza et al. | |
| 2018/0154118 A1 * | 6/2018 | Kyvik .................... | A61M 25/02 |
| 2018/0228699 A1 * | 8/2018 | Oliveira .............. | A61J 15/0061 |
| 2018/0235845 A1 * | 8/2018 | Oliveira .............. | A61J 15/0003 |
| 2020/0078561 A1 * | 3/2020 | Oliveira ............... | A61M 25/02 |
| 2021/0077782 A1 * | 3/2021 | Beran ................... | A61M 25/02 |
| 2022/0134057 A1 * | 5/2022 | Beran ................... | A61M 25/02 604/179 |

FOREIGN PATENT DOCUMENTS

| | | |
|---|---|---|
| WO | 2007118636 A1 | 10/2007 |
| WO | 2010056541 A1 | 5/2010 |
| WO | 2010056543 A1 | 5/2010 |
| WO | 2012018402 A1 | 2/2012 |
| WO | 2014036346 A1 | 3/2014 |
| WO | 2014036348 A1 | 3/2014 |
| WO | 2014099709 A1 | 6/2014 |
| WO | 2014149718 A1 | 9/2014 |
| WO | 2019073326 A1 | 4/2019 |
| WO | 2020201879 A1 | 10/2020 |
| WO | 2020240362 A1 | 12/2020 |
| WO | 2021069995 A1 | 4/2021 |

* cited by examiner

TUBE SECUREMENT TAPE

CROSS REFERENCE TO RELATED APPLICATIONS

This application is a national stage filing under 35 U.S.C. 371 of PCT/IB2020/059861, filed Oct. 20, 2020, which claims the benefit of U.S. Provisional Application No. 62/927,250, filed Oct. 29, 2019, the disclosures of which are incorporated by reference in its entirety herein.

TECHNICAL FIELD

The present disclosure generally relates to medical article securement systems and methods for securing medical articles to the body of a patient, and particularly, for securing various catheter systems, tubes, or other elongated devices to the body of a patient.

BACKGROUND

Tubes and catheters are inserted through a patient's skin to either introduce fluids to the patient or to remove fluids from the patient. The tubes must be secured to prevent the tube from slipping out of the patient. Commonly, surgical tape is used to hold tubing to the patient's skin.

One very common type of tube is an intravenous (IV) catheter. An IV catheter is inserted into the patient's bloodstream. Movement of an IV catheter while the catheter is inserted in a vein is a leading cause of catheter failure. When a catheter moves in a vein, it scrapes and pokes the inner wall of the vein, thereby irritating the vein. Repeated movement of the catheter can cause enough irritation of the vein to require that the catheter be removed and then a new catheter to be inserted in a different location along the same vein or in an entirely different vein. Therefore, a need exists for effective securement systems for catheters.

SUMMARY

The disclosed securement tape strip comprises a tape having a midsection, a stabilizing section, and a wrapping strip. The tape strip has an adhesive along the midsection to adhere the tape strip to a substrate. The wrapping strip can include an adhesive for wrapping the wrapping strip around a device to hold the device securely in place on the substrate. The tape strip includes a perforation set extending along the midsection. The perforation set can be useful in removal of the tape.

In one embodiment, the tape strip includes a first major surface and a second major surface opposite the first major surface and a perimeter surrounding a body layer. The body layer has a midsection extending through the body layer from a first point on the perimeter to a second point on the perimeter. A stabilizing section extends from the midsection, and a first wrapping strip extends from the midsection, with a first cut through the body layer separating the first wrapping strip from the stabilizing section. A perforation set extends through the body layer at the midsection, extending from the first point on the perimeter to the second point on the perimeter. An adhesive is disposed on the first major surface. In some embodiments, an adhesive is disposed on the second major surface at the first wrapping strip.

In some embodiments the adhesive disposed on the first major surface is a flood coating. In some embodiments, the adhesive disposed on the first major surface is a pattern coating.

In a further embodiment, the tape strip includes a second wrapping strip extending from the midsection. In some embodiments, an adhesive is disposed on the second major surface at the second wrapping strip.

In another embodiment, a dressing system is provided that includes a cover dressing and a tape strip of the present disclosure, wherein the cover dressing overlies at least a portion of the tape strip.

In another embodiment, a method of securing a device to a substrate is provided, including applying adhesive at the midsection of a tape strip of the present disclosure to a substrate and under a device, and wrapping the wrapping strip(s) of the tape strip around the device, thereby securing the device to the substrate.

In another embodiment, the tape strip includes a first major surface and a second major surface opposite the first major surface and a perimeter surrounding a body layer. The body layer has a midsection extending through the body layer from a first point on the perimeter to a second point on the perimeter. A stabilizing section extends from the midsection, and a first wrapping strip extends from the midsection, with a first cut through the body layer separating the first wrapping strip from the stabilizing section. An adhesive is disposed on the second major surface at the first wrapping strip. In some embodiments a second wrapping strip extends from the midsection, and an adhesive is disposed on the second major surface at the second wrapping strip.

DETAILED DESCRIPTION

Tape Strip

Figure 1:
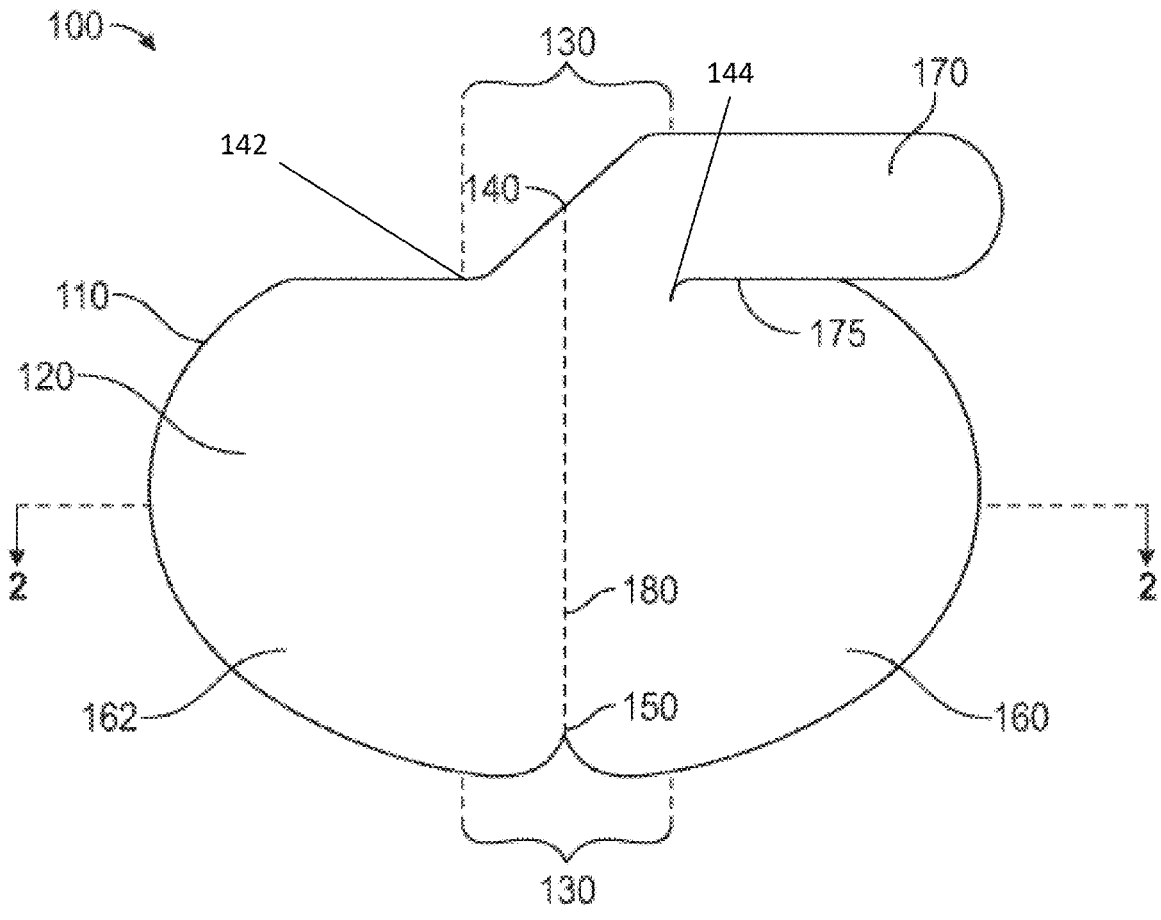
FIG. 1 is an embodiment of a tape strip of the present disclosure.

The disclosed tape strip 100 secures a device, for example, tubing, to a substrate. Referring to FIG. 1, tape strip 100 has perimeter 110 surrounding body layer 120, a midsection 130 extending from a first point 140 on the perimeter to a second point 150 on the perimeter, through body layer 120. First stabilizing section 160 extends from midsection 130 in a first direction, and second stabilizing section 162 extend from midsection 130 in a second direction, opposite the first direction. A first wrapping strip 170 extends from midsection 130 in the first direction, separated from first stabilizing section 160 by first cut 175. A perforation set 180 extends through body layer 120 at midsection 130, extending from first point 140 to second point 150 along an axis. In some embodiments, the first wrapping strip 170 extends from the body layer 120 from a first origin point 142 on a first side of the axis and a second origin point 144 on a second side of the axis.

Figure 2:
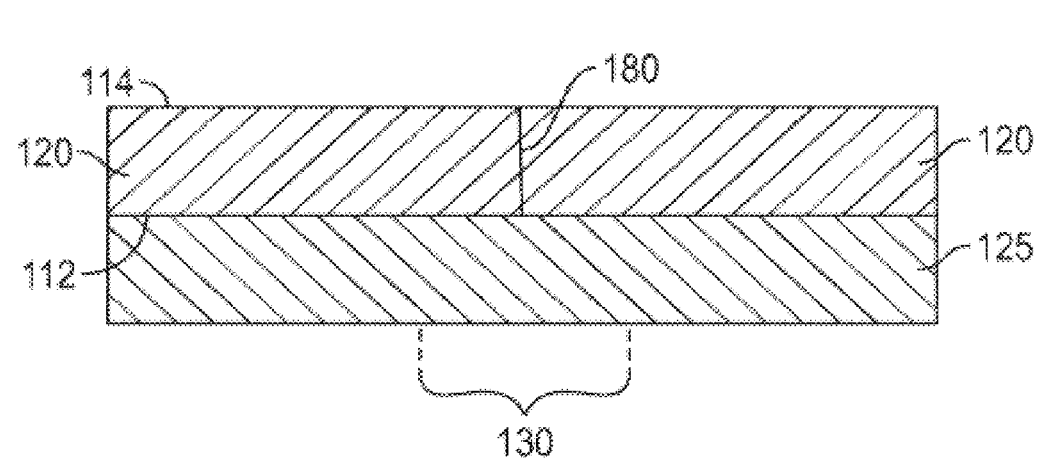
FIG. 2 is a side-sectional view of FIG. 1 through line 2-2.

FIG. 2 shows a side-sectional view of FIG. 1 through line 2-2, showing tape strip 100 with body layer 120 having first major surface 112 and second major surface 114 opposite first major surface 112. A layer of adhesive 125 is disposed on first major surface 112 of body layer 120. A perforation set 180 extends through midsection 130 from second major surface 114 to first major surface 112, and optionally through the layer of adhesive 125. In some embodiments, a layer of adhesive 125 is disposed on second major surface 114 at the midsection 130 at first wrapping strip 170. Including adhesive 125 in the portions that would underly a device adds stability of the secured device to the substrate.

In some embodiments, the layer of adhesive 125 is a continuous flood coating on body layer 120. In some embodiments, the layer of adhesive 125 is a continuous pattern coating on body layer 120. The selection of flood coating versus pattern coating can depend, for example, on a selection of a moisture-vapor transmission rate for the tape strip.

Figure 3:
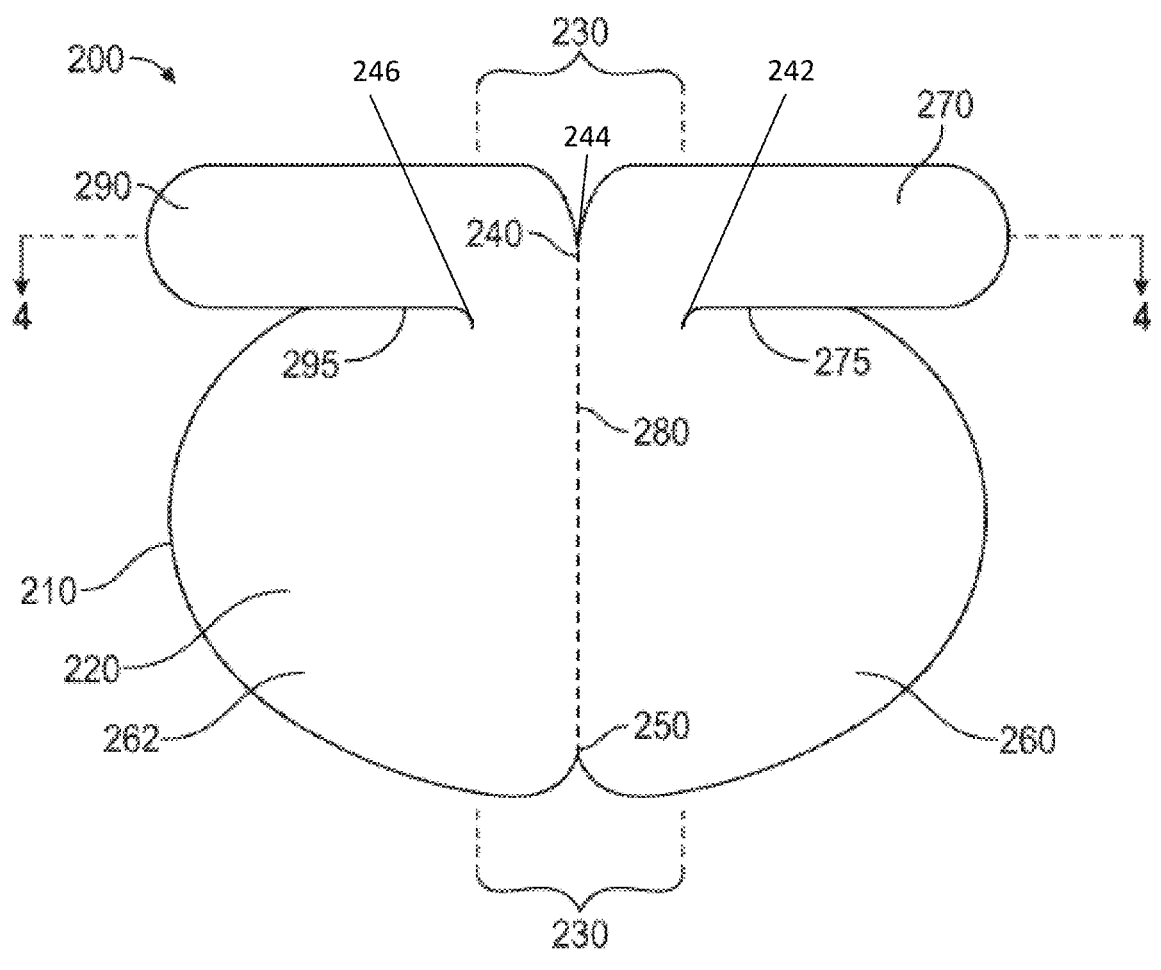
FIG. 3 is an embodiment of a tape strip of the present disclosure.

FIG. 3 shows a further embodiment of a tape strip of the disclosure, similar to tape 100 but with an added wrapping strip for enhanced securement of, for example, a tube. Accordingly, tape strip 200 has perimeter 210 surrounding body layer 220, a midsection 230 extending from a first point 240 on the perimeter to a second point 250 on the perimeter, through body layer 220. First stabilizing section 260 and second stabilizing section 262 extend from midsection 230 in first and second directions, respectively. A first wrapping strip 270 extends from midsection 230 in the first direction, separated from first stabilizing section 260 by first cut 275. In tape strip 200, a second wrapping strip 290 extends from midsection 230 in the second direction, separate from second stabilizing section 262 by second cut 295. In some embodiments, an adhesive is disposed on the second major surface at first wrapping strip 270 and at second wrapping strip 290. A perforation set 280 extends through body layer 220 at midsection 230, extending from first point 240 to second point 250 along an axis. In some embodiments, the first wrapping strip 270 extends from the body layer 220 from a first origin point 242 on a first side of the axis and a second origin point 244 aligned with the axis, while the second wrapping strip 290 extends from the body layer 220 from a third origin point 246 on a second side of the axis and the second origin point 244.

In some embodiments, first wrapping strip 270 and second wrapping strip 290 extend in equal lengths from midsection 230. In some other embodiments, first wrapping strip 270 and second wrapping strip 290 extend in unequal lengths from midsection 230. In some embodiments, first wrapping strip 270 and second wrapping strip 290 both extend from midsection 230 in essentially opposite direction that are perpendicular to an axis that includes first point 240 and second point 250. In some other embodiments, the wrapping strips extend on opposite sides of midsection 230, but not in entirely opposite directions. For example, either the first or the second wrapping strip may extend from midsection 230 with an angle of anywhere between 0 degrees and 180 degrees with respect to an axis that includes first point 240 and second point 250. In these instances, either or both of cuts 275 and 295 may define an angle wider than 0 degrees between wrapping strip and stabilizing section. In some embodiments, cuts 275 and 295 have geometries that can be other than a straight line; for example, the cuts may be curved, a sawtooth pattern, or any other geometry suitable for giving a separation between the wrapping strip and the corresponding stabilizing section. In some embodiments, there may be more than one cut to separate the wrapping strip from the stabilizing section. In some embodiments, a line of perforations between the wrapping strip and the stabilizing sections can be used to permit manual tearing to effectively form a cut. The selection of various wrapping strip lengths, angles, and geometries of the cuts may be useful, for example, in providing optimal securement for any of a variety of devices.

Figure 4:
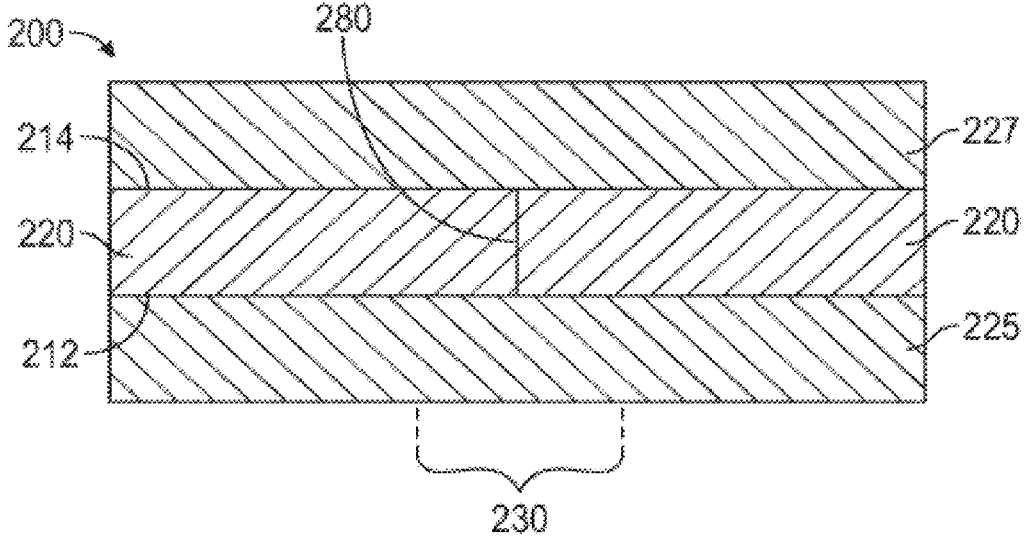
FIG. 4 is a side-sectional view of FIG. 3 through line 4-4.

FIG. 4 shows a side-sectional view of FIG. 3 through line 4-4, showing midsection 230, first wrapping strip 270, and second wrapping strip 290, and viewing along perforation set 280 towards first point 240. FIG. 4 shows tape strip 200 with body layer 220 having first major surface 212 and second major surface 214 opposite first major surface 212. In the embodiment shown, body layer 220 has a layer of adhesive 225 disposed on first major surface 212. Also, in this embodiment, body layer 220 has a layer of adhesive 227 disposed on second major surface 214. The layer of adhesive 227 is disposed on second major surface 214 at first wrapping strip 270 and at second wrapping strip 290. providing for adhesion to a device and for adhesion of the wrapping strips as one overlies the other.

Also, shown in FIG. 4, perforation set 280 through midsection 230 extends from second major surface 214 to first major surface 212. The perforation set can optionally extend through one or both of adhesive layers 225 and 227.

Perforation sets 180 and 280 are included to facilitate, for example, tearing the tape strip apart along the midsection. Once the tape strip is torn along the midsection, it can more readily be separated from the substrate and from a secured tube.

Figure 5:
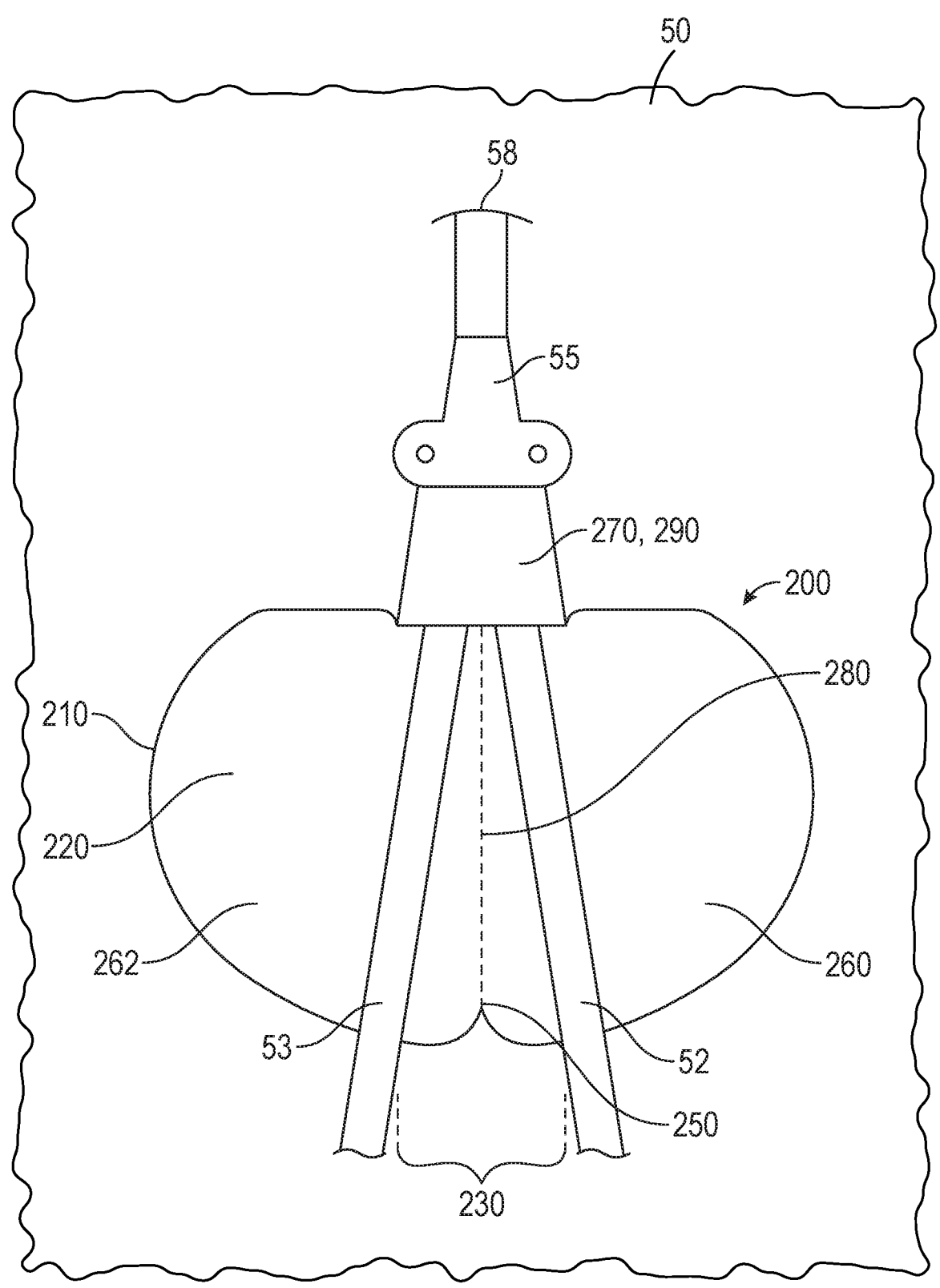
FIG. 5 is an embodiment of a tape strip of the present disclosure with a secured tube.

FIG. 5 shows an embodiment of the tape strip 200 securing a device to a substrate 50. The device, in this instance, is catheter 55, is inserted into a substrate 50 at insertion point 58. Catheter 55 includes tubes 52 and 53, for adding: and removing fluids through catheter 55. However, catheter 55 is non-limiting with respect to devices that can be secured by tape strips of the present disclosure. In some embodiments, midsection 230, first stabilizing section 260, and second stabilizing section 262 are all applied to substrate 50, with catheter 55 positioned over midsection 230. First wrapping strip 270 and second wrapping strip 290 are each wrapped one over the other and around catheter 55, providing securement of catheter 55. In some embodiments the wrapping strips are overlapping. while in some other embodiments, the wrapping strips are non-overlapping.

Figure 6:
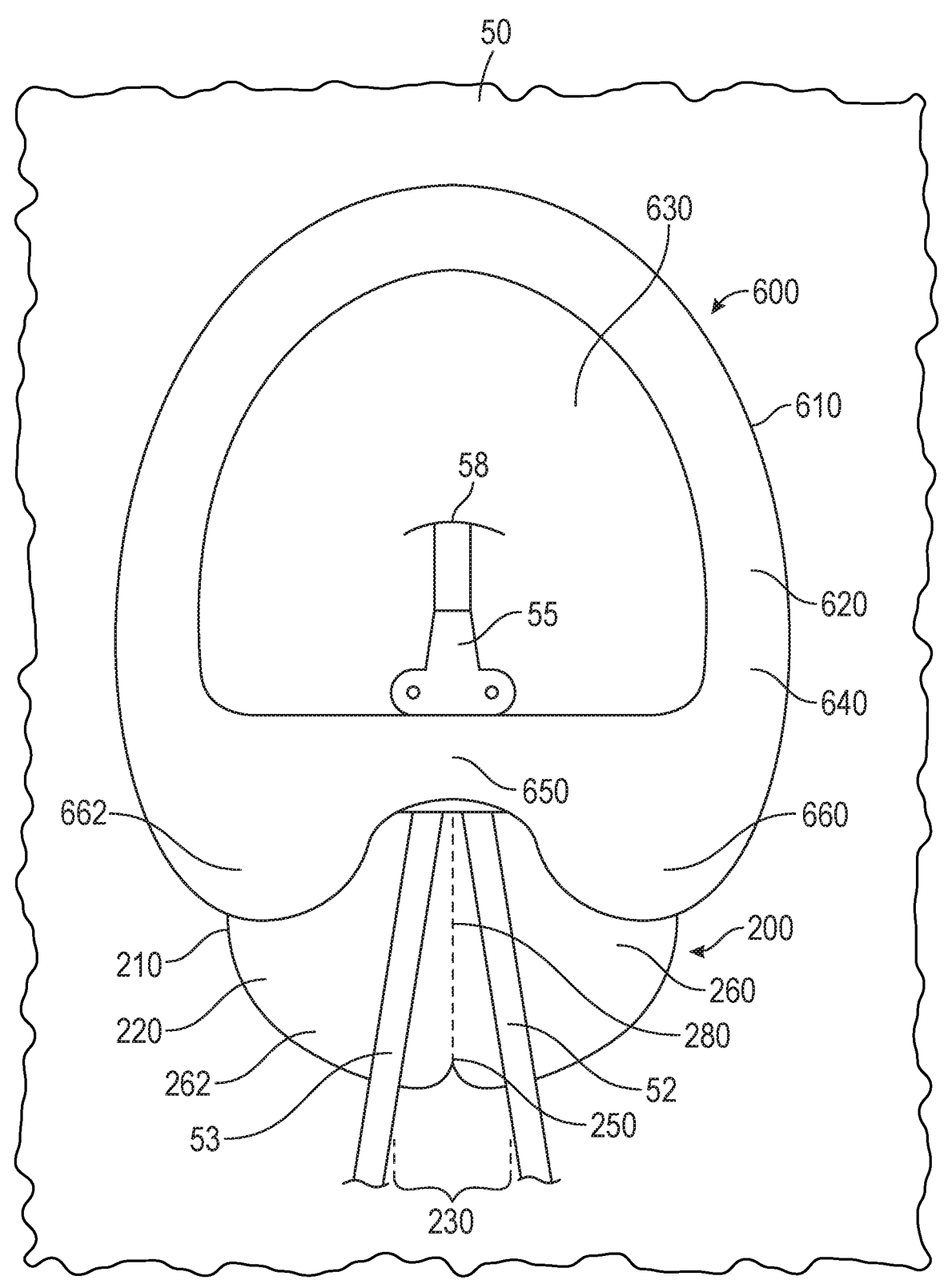
FIG. 6 is an embodiment of a tape strip of the present disclosure with a secured tube and a cover dressing.

FIG. 6 shows an embodiment of a cover dressing 600 overlying the tape strip 200 and secured catheter 55 from FIG. 5 (labels 210, 220, 230, 250, 260, 262, and 280 on tape strip 200 each designate the same part as in FIG. 5). Cover dressing 600 has a first major surface, a second major surface opposite the first major surface, defined by a perimeter 610 around a body layer 620, the second major surface optionally comprising an adhesive. In FIG. 6, the second major surface of dressing 600 overlies substrate 50. Dressing 600 includes a film 630 which is sufficiently transparent to permit visual inspection of catheter 55 and insertion point 58. In some embodiments, at least a portion of film 630 extends to perimeter 610. In some embodiments, dressing 600 includes a support layer 640, which in this embodiment extends to perimeter 610, and defines a central window to permit a view through film 630, in order to visually inspect catheter 55 and insertion point 58. In some embodiments, dressing 600 does not include a support layer. The wrapping strips 270 and 290 are shown in FIG. 5 as being wrapped around catheter 55. However, in FIG. 6, the wrapping tapes are not shown, since they are covered by support layer 640 at a bridging area 650. Cover dressing 600 can optionally include tabs 660 and 662, shown as overlying first and second stabilizing regions 260 and 262, respectively, and in this way the adhesive on the second major surface of cover dressing 600 overlies tape strip 200, for enhanced overall securement of catheter 55. In embodiments where device 55 is an IV catheter inserted into a vein, the cover dressing can beneficially provide a physical protection of the insertion site from fluids, particulates, microorganisms, and the like.

Each of perforation sets 180 and 280 is a set of through cuts with each cut separate from another cut by the body layer. The cuts of the perforation set extend at least partially through the thickness of the body layer to create an area of structural weakness of the body layer. In some embodiments, the through cuts of the perforation set extend entirely through the body layer. In some embodiments, the through cuts extend partially into the body layer. If the body layer is a multilayer construction, the through cuts could extend entirely through one layer, and not through other layers of the body layer. In one some embodiments, the cut of the perforation set is a slit with essentially no width, meaning: no material was removed from the body layer during cutting. In one embodiment, the cut of the perforation set is a width of material removed.

The individual cuts may be the same length as one another or may be of varying lengths. For example, the length of individual cuts may graduate from shorter to longer or from longer to shorter. The same with spacing between individual cuts, which may be the same length as one another or may be of varying lengths. For example, the spacing between the individual cuts may graduate from shorter to longer or from longer to shorter.

In some embodiments, the perforation set 180 in tape strip 100 extends across the body layer from first point 140 to second point 150. In another embodiment, the perforation set 180 extends only partially between first point 140 and second point 150; that is, perforation set can start from either first point 140 or second point 150 and extend only part way across the body layer or can extend between first point 140 and second point 150 without reaching perimeter 110 at either end. The perforation set can be in a line, an array, or cluster. If the first perforation set is in a line, it can be straight, angled, or curved. An analogous configuration of the perforation set applies for tape strip 200.

In some embodiments, the perforation set has cut lengths between about 0.5 mm to about 25 mm. In some embodiments, the perforation set has length of the body layer separating the cuts between about 0.3 mm to about 1.3 mm.

The perforation set of the disclosure can be an area of structural weakness, facilitating manual tearing of the tape. In some other embodiments, a tape of the disclosure does not include a perforation set. In either case, the midsection can include structural weakness achieved by, for example, selection of a weaker material for the area, selection of a thinner portion of the body layer for the area, or a combination of these, to facilitate manual tearing along the midsection.

Backing Material

The tape strip body layer includes a backing layer that can be any material that provides mechanical stiffening of the tape while also allowing enough flexibility to allow for conformability and comfortable wear. Backing material can be a film, a paper, or a fabric layer material, such as a woven, knitted, or nonwoven fabric. Backing material can be elastic or stiff. In some embodiments, the backing layer material is a woven, knitted, or nonwoven material. One example of a nonwoven material is a high strength nonwoven fabric available from E.I. Dupont de Nemours & Company of Wilmington, Del., under the trademark SONTARA. Other suitable nonwoven webs include a hydroentangled polyester fabric available from Vertac, a division of International Paper of Walpole, Minn. Another suitable nonwoven web is the nonwoven elastomeric web described in U.S. Pat. No. 5,230,701. The backing can be a high moisture vapor permeable film backing. U.S. Pat. No. 3,645,835 describes methods of making such films and methods for testing their permeability.

The backing may be a single layer or multilayer construction. In some embodiments, reinforcing materials may be included with the backing. The reinforcing material may be as pliable as a thick adhesive or as stiff as a solid material (e.g., a paper or a film). As a further example of a backing, U.S. Pat. No. 5,088,483 discloses a permanent adhesive as a securing material.

Adhesive

Any number of adhesives can be used with the tape and on the dressing, if included. Suitable adhesives are pressure sensitive and in certain embodiments have a relatively high moisture vapor transmission rate to allow for moisture evaporation. Suitable pressure sensitive adhesives include those based on acrylates, urethane, hydrogels, hydrocolloids, block copolymers, silicones, rubber-based adhesives (including natural rubber, polyisoprene, polyisobutylene, butyl rubber etc.) as well as combinations of these adhesives. The adhesive component may contain tackifiers, plasticizers, rheology modifiers as well as active components, for example an antimicrobial agent.

The pressure sensitive adhesive is usually reasonably skin compatible and "hypoallergenic", such as the acrylate copolymers described in U.S. Pat. No. RE 24,906. Particularly useful is a 97:3 iso-octyl acrylate:acrylamide copolymer, as is 70:15:15 isooctyl acrylate:ethyleneoxide acrylate:acrylic acid terpolymer described in U.S. Pat. No. 4,737,410. Additional useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

Silicone adhesives can also be used. Generally, silicone adhesives can provide suitable adhesion to skin while gently removing from skin. Suitable silicone adhesives are disclosed in PCT Publications WO2010/056541 and WO2010/056543, the disclosures of which are incorporated herein by reference.

Adhesive layers of the present disclosure can be flood-coated, or pattern-coated. A patterned-coated adhesive layer typically allows for better vapor transmission. An example of useful pattern coating is described in U.S. Pat. No. 4,595,001.

Dressing

In some embodiments, suitable dressings of the present disclosure typically include a thin, flexible and transparent polymeric film body layer and a support material. In general, the support layer materials can include, but are not limited to, an elastic film, a non-elastic film, nonwoven fibrous web, woven fibrous web, knits, and polyethylene/vinyl acetate copolymer-coated papers and polyester films. Examples of suitable dressings can be found, for example, in PCT Publication WO2019/073326 and U.S. Patent Application Pub. No. US2016/0015570. One example of a commercially available medical dressing is TEGADERM IV ADVANCED DRESSING (3M Co., St. Paul, Minn.).

Release Liner

In some embodiments, tapes and dressings of the present disclosure include a release liner film disposed on the adhesive layer (for example, adhesive layer 125 in FIG. 2). Release liners can be made of kraft papers, polyethylene, polypropylene, polyester or composites of any of these materials. The films are preferably coated with release agents such as fluorochemicals or silicones. For example, U.S. Pat. No. 4,472,480, the disclosure of which is hereby incorporated by reference, describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by Loparex Group (Willowbrook, Ill.).

In some embodiments, the disclosed tape strips and cover dressings can be included together on a sheet of release liner, providing a convenient kit of these components.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. A tape strip comprising:
   a body layer, comprising:
   a midsection;
   a first stabilizing section extending in a first direction from the midsection; and
   a second stabilizing section extending in a second direction from the midsection;
   a perforation set defined in the body layer, wherein the perforation set extends along an axis;
   a wrapping strip extending from the body layer, the wrapping strip including:
   a first edge extending from the body layer at a first origin point on a first side of the axis;
   a second edge extending transversely from the first edge;
   a third edge extending from the body layer at a second origin point on a second side of the axis; and
   an arcuate edge extending between and connecting the second and third edges; and
   an adhesive disposed on the body layer to adhere the body layer to a substrate;
   wherein the wrapping strip is foldable across the axis to wrap about at least a portion of a perimeter of a device.

2. The tape strip of claim 1, wherein the adhesive disposed on the body layer is a continuous pattern coating.

3. The tape strip of claim 1, wherein the adhesive is a first adhesive, and wherein the tape strip further comprises a second adhesive disposed on the wrapping strip to adhere the wrapping strip to the device.

4. The tape strip of claim 1, further comprising a cover dressing.

5. The tape strip of claim 1, wherein the first edge extends across the axis.

6. A method of securing a device to a substrate, wherein the method comprises:
   adhering the tape strip of claim 1 to the substrate with the adhesive;
   positioning at least a portion of the device on the body layer; and
   wrapping the wrapping strip around at least a portion of the perimeter of the device.

7. The method of claim 6, further comprising:
   applying a cover dressing over at least a portion of the tape strip, the cover dressing comprising:
   a first major surface, a second major surface opposite the first major surface defined by a perimeter around a body layer, wherein an adhesive is disposed on the second major surface, the second major surface overlying the substrate.

8. The method of claim 6, wherein the adhesive is a first adhesive, and wherein the method further comprises adhering the wrapping strip to the device with a second adhesive disposed on the wrapping strip.

9. The tape strip of claim 1,
   wherein the wrapping strip comprises:
   an adhesive; and
   a release liner removably covering the adhesive on the wrapping strip.

10. A tape strip comprising:
   a body layer;
   a perforation set defined in the body layer, wherein the perforation set extends along an axis;
   an adhesive to adhere the body layer to a substrate; and
   a wrapping strip extending from the body layer, wherein the wrapping strip is foldable laterally across the axis to wrap about at least a portion of a perimeter of a device, wherein the wrapping strip includes;
   a first edge extending from the body layer at a first origin point on a first side of the axis;
   a second edge extending transversely from the first edge;
   a third edge extending from the body layer at a second origin point on a second side of the axis; and
   an arcuate edge extending and connecting the second and third edges.

11. The tape strip of claim 10, wherein the adhesive is a first adhesive, and wherein the tape strip further comprises a second adhesive disposed on the wrapping strip to adhere the wrapping strip to the device.

12. The tape strip of claim 10, wherein the first edge extends across the axis.

\* \* \* \* \*